US012026981B2

(12) United States Patent
Chono et al.

(10) Patent No.: US 12,026,981 B2
(45) Date of Patent: Jul. 2, 2024

(54) IMAGE PROCESSING APPARATUS, METHOD, SYSTEM, AND COMPUTER READABLE MEDIUM

(71) Applicant: NEC Corporation, Tokyo (JP)

(72) Inventors: Keiichi Chono, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 93 days.

(21) Appl. No.: 17/431,542

(22) PCT Filed: Feb. 12, 2020

(86) PCT No.: PCT/JP2020/005219
§ 371 (c)(1),
(2) Date: Aug. 17, 2021

(87) PCT Pub. No.: WO2020/170893
PCT Pub. Date: Aug. 27, 2020

(65) Prior Publication Data
US 2022/0139111 A1     May 5, 2022

(30) Foreign Application Priority Data

Feb. 18, 2019   (JP) ................................ 2019-026939

(51) Int. Cl.
*G06V 40/19*  (2022.01)
*G06T 7/20*   (2017.01)
(Continued)

(52) U.S. Cl.
CPC ................ *G06V 40/19* (2022.01); *G06T 7/20* (2013.01); *G06V 10/141* (2022.01); *G06V 10/25* (2022.01);
(Continued)

(58) Field of Classification Search
None
See application file for complete search history.

(56) References Cited

U.S. PATENT DOCUMENTS

2005/0084179 A1 *   4/2005   Hanna ................... G06V 40/19
                                                    382/294
2008/0199054 A1     8/2008   Matey
(Continued)

FOREIGN PATENT DOCUMENTS

CN      104967803 B  *  1/2018
JP      2002118822 A *  4/2002
(Continued)

OTHER PUBLICATIONS

International Search Report for PCT Application No. PCT/JP2020/005219, dated Apr. 14, 2020.
(Continued)

*Primary Examiner* — Shadan E Haghani

(57) ABSTRACT

Iris image pick-up devices perform image pick-up of an iris of a moving subject. Images from the iris image pick-up devices are written to storage areas for transfer in a memory. A readout device reads out an image stored in the storage areas for transfer to a storage area for image processing at a frame interval corresponding to the movement speed of the subject. An image processing unit executes processing using the image read out to the storage area for image processing.

7 Claims, 6 Drawing Sheets

(51) Int. Cl.
| | | |
|---|---|---|
| G06V 10/141 | (2022.01) |
| G06V 10/25 | (2022.01) |
| G06V 40/60 | (2022.01) |
| H04N 23/56 | (2023.01) |
| H04N 23/80 | (2023.01) |
| H04N 23/90 | (2023.01) |

(52) U.S. Cl.
 CPC ............ *G06V 40/67* (2022.01); *H04N 23/56* (2023.01); *H04N 23/80* (2023.01); *H04N 23/90* (2023.01); *G06T 2207/30196* (2013.01)

(56) References Cited

U.S. PATENT DOCUMENTS

| | | | |
|---|---|---|---|
| 2010/0290668 A1 | 11/2010 | Friedman et al. | |
| 2010/0299530 A1* | 11/2010 | Bell | G06V 40/18 382/117 |
| 2012/0019655 A1 | 1/2012 | Fukamachi et al. | |
| 2012/0081580 A1 | 4/2012 | Cote et al. | |
| 2017/0180589 A1* | 6/2017 | Guo | H04N 5/772 |
| 2020/0026831 A1* | 1/2020 | Alameh | G06V 40/19 |

FOREIGN PATENT DOCUMENTS

| | | | |
|---|---|---|---|
| JP | 2007504562 A | | 3/2007 |
| JP | 2007-148988 A | | 6/2007 |
| JP | 2009217526 A | * | 9/2009 |
| JP | 2010-134735 A | | 6/2010 |
| SG | 11202108903 R | | 9/2021 |
| SG | 11202108917 P | | 9/2021 |
| WO | 2008152767 A1 | | 12/2008 |
| WO | 2009016846 A1 | | 2/2009 |

OTHER PUBLICATIONS

Masahiko Hosoya, "Identification System by Iris Recognition", Transactions of the Japanese Society for Medical and Biological Engineering 44(1), pp. 33-39, 2006.
John Daugman, "How Iris Recognition Works", pp. 1-10, [Online] <URL: https://www.cl.cam.ac.uk/~jgd1000/irisrecog.pdf>.
Extended European Search Report for EP Application No. 20759896.2 dated Mar. 15, 2022.
JP Office Action for JP Application No. 2021-501881, dated Sep. 13, 2022 with English Translation.
Singapore Office Action for SG Application No. 11202108901P dated Feb. 20, 2023.
IN Office Communication for IN Application No. 202147041178, mailed on Apr. 25, 2024.

* cited by examiner

IMAGE PROCESSING APPARATUS, METHOD, SYSTEM, AND COMPUTER READABLE MEDIUM

This application is a National Stage Entry of PCT/JP2020/005219 filed on Feb. 12, 2020, which claims priority from Japanese Patent Application 2019-026939 filed on Feb. 18, 2019, the contents of all of which are incorporated herein by reference, in their entirety.

TECHNICAL FIELD

The present disclosure relates to an image processing apparatus, a method, a system, and a computer readable medium, and in particular to an image processing apparatus, a method, a system, and a program that can be used for authentication using an iris(es).

BACKGROUND ART

Biometric authentication using an iris(es) has been known. In such biometric authentication, iris(es) of a subject is photographed by using an image pick-up apparatus, and feature values are extracted from the pattern of the photographed iris. In order to authenticate a subject, extracted feature values are compared with those registered in advance in a database, and a pass/fail is determined based on a score of matching therebetween. Further, in order to register a subject to be authenticated, extracted feature values are added in the database.

As described in Non-patent Literature 1, an iris, which is a donut-shaped tissue surrounding a pupil, has a very complex pattern, and is unique to each person. Further, in the photographing of an iris, near-infrared light is applied to eyes of a subject.

As described in Non-patent Literature 2, in the photographing of an iris(es), an image of the iris is taken with a resolution in which the radius of the iris is expressed by 100 to 140 pixels. Further, the wavelength of the near-infrared light applied to the eyes of the subject is in a range between 700 nm and 900 nm.

CITATION LIST

Non Patent Literature

Non-patent Literature 1: Hosoya, "Identification System by Iris Recognition", Japanese Society for Medical and Biological Engineering 44(1), pages 33-39, 2006
Non-patent Literature 2: Daugman, "How Iris Recognition Works," https://www.cl.cam.ac.uk/~jgd1000/irisrecog.pdf

SUMMARY OF INVENTION

Technical Problem

The diameter of an iris is about 1 cm. Therefore, when the radius of an iris is expressed by 100 pixels, the granularity becomes 50 μm. Since the pattern of an iris is microscopic as described above, it is difficult to photograph an iris pattern at a level of quality sufficient for authentication and verification under conditions that distance between the subject and the image pick-up means is large, a field of view to be photographed is wide, and the subject moves.

In light of the above circumstances, an object of the present disclosure is to provide an image processing apparatus, method, system, and computer-readable medium capable of photographing an iris pattern at a level of quality sufficient for authentication and verification.

Solution to Problem

In order to achieve the above-described object, in a first aspect, the present disclosure provides an image processing system including:
a plurality of iris image pick-up means disposed at mutually different positions in the same field of view;
overall image pick-up means for performing image pick-up over a wider field of view than the field of view of the iris image pick-up means;
guiding means for guiding a subject;
illumination means for illuminating the subject with light; and
control means for controlling, using an image from the overall image pick-up means, at least one of reading out an image from the plurality of iris image pick-up means, presenting at least one of an image and a sound through the guiding means, or providing illumination with light from the illumination means, wherein
the control means includes readout means for reading out an image written to a storage area for transfer from the iris image pick-up means to a storage area for image processing at a frame interval corresponding to a movement speed of the subject, and image processing means for executing processing using the image read out to the storage area for image processing.

In a second aspect, the present disclosure provides an image processing apparatus including:
readout means for reading out an image written to a storage area for transfer from iris image pick-up means for performing image pick-up of an iris of a moving subject to a storage area for image processing at a frame interval corresponding to a movement speed of the subject; and
image processing means for executing processing using the image read out to the storage area for image processing.

In a third aspect, the present disclosure provides an image processing method including:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a fourth aspect, the present disclosure provides an image processing method including:
reading out an image written to a storage area for transfer from iris image pick-up means for performing image pick-up of an iris of a moving subject to a storage area for image processing at a frame interval corresponding to a movement speed of the subject; and
executing processing using the image read out to the storage area for image processing.

In a fifth aspect, the present disclosure provides a non-transitory computer readable medium storing a program causing a computer to execute a process including:
performing, using an image from overall image pick-up means for performing image pick-up over a wider field of view than a field of view of a plurality of iris image pick-up means disposed at mutually different positions in the same field of view, at least one of reading out an image from the plurality of iris image pick-up means, presenting at least one of an image and a sound through guiding means for guiding a subject, or providing illumination with light from illumination means for illuminating the subject with light.

In a sixth aspect, the present disclosure provides a non-transitory computer readable medium storing a program causing a computer to execute a process including:

reading out an image written to a storage area for transfer from iris image pick-up means for performing image pick-up of an iris of a moving subject to a storage area for image processing at a frame interval corresponding to a movement speed of the subject; and executing processing using the image read out to the storage area for image processing.

Advantageous Effects of Invention

An image processing apparatus, a method, a system, and a computer readable medium according to the present disclosure is capable of photographing an iris pattern at a level of quality sufficient for authentication and verification.

DESCRIPTION OF EMBODIMENTS

Prior to giving the description of an example embodiment according to the present disclosure, a problem thereof is quantitatively described. As an example, the below-shown conditions, which are assumed as operational conditions for Automated Border Control systems (ABC systems) and the like, will be described hereinafter. It is assumed that a distance between a subject and image pick-up means (the distance between a subject and a gate) is 2 m, and a horizontal field of view, i.e., a range in the horizontal direction in which both eyes of one subject can be covered, is 0.2 m. Further, a vertical field of view, i.e., a range in the vertical direction in which the eyes of a wide range of subjects from a tall subject, typically a male person, to a short subject, typically a female person, can be covered, is 0.4 m. Further, it is assumed that the walking speed (the moving speed) of the subject relative to the gate is equal to the average of slow walking speeds of adult people, e.g., is 1 m/s.

Under the above operating conditions, assuming that an image sensor with a pixel pitch of 5 μm and a lens with an aperture stop of F2 and a focal length of 200 mm are used, both a high resolution of 32 M pixels and a high frame rate of 100 frames per second (fps) are demanded from the image pick-up means, as described later.

With regard to resolution, to secure a 0.2 m horizontal field of view at a position 2 m away from the image pick-up apparatus, the image pick-up apparatus needs 4000 pixels (0.2 [m]÷50 [μm]=4000) in the horizontal direction. Further, to secure a 0.4 m vertical field of view at a position 2 m away from the image pick-up apparatus, the image pick-up apparatus needs 8000 pixels (0.4 [m]÷50 [μm]=8000) in the vertical direction. As a result, a resolution of 32 M pixels is demanded from the image pick-up apparatus.

On the other hand, in the case where the above lens is used, if the allowable circle of confusion diameter is 0.03 mm, the depth of field that can be secured 2 m away is approximately 1 cm. In the case where the subject has a walking speed of 1 m/s, the time it takes for the subject to pass through the 1 cm subject depth is 1 [cm]÷100 [cm/s] =0.01 s. In this case, to capture the 0.01 s instant when the iris of the walking subject is in focus, a performance of 100 fps (1 [s]÷100 [fps]=0.01 s time resolution) is demanded from the image pick-up apparatus.

Image pick-up equipment capable of satisfying a high resolution of 32 M pixels and a high frame rate of 100 fps with a single device does not exist as a popular product. Consequently, photographing an iris pattern at a level of quality sufficient for authentication and verification under the operating conditions described above is difficult. This concludes the quantitative description of the problem.

Figure 1:
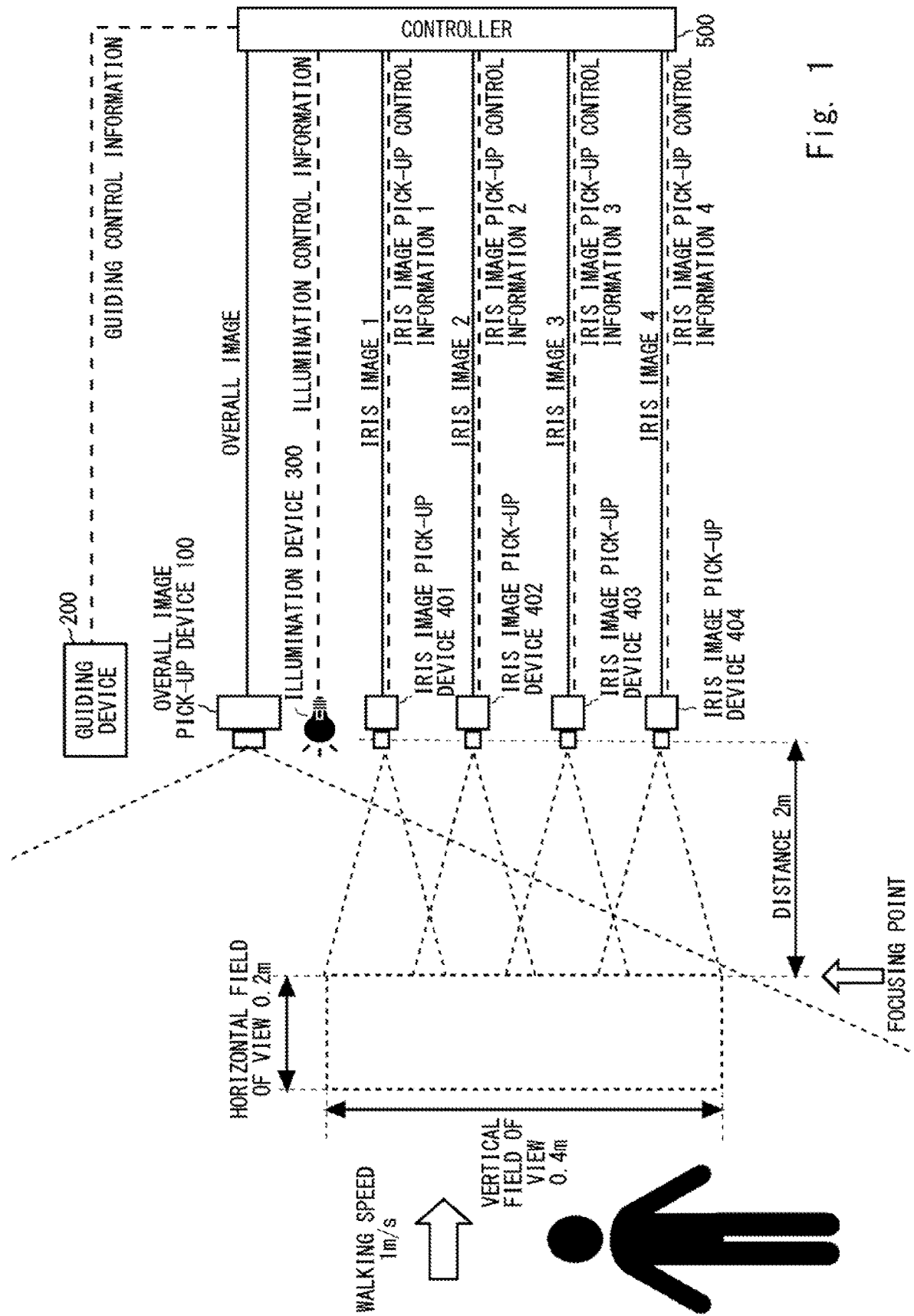
FIG. 1 is a block diagram showing an image processing system according to a first example embodiment of the present disclosure.

Example embodiments according to the present disclosure will be described hereinafter with reference to the drawings. FIG. 1 shows an image pick-up system according to a first example embodiment of the present disclosure. The image processing system includes an overall imaging device 100, a guiding device 200, an illumination device 300, iris image pick-up devices 401 to 404, and a controller 500. Note that although the number of iris image pick-up devices is four in FIG. 1, the number of iris image pick-up devices is not limited to any particular number. The number of iris image pick-up devices can be set as appropriate according to the field of view to be covered and the resolutions of available iris image pick-up devices.

The overall imaging device (overall image pick-up means) 100 photographs a subject with a wide field of view that is wide enough to cover a whole range of subjects from a tall subject to a short subject. The overall imaging device 100 may have a resolution in which a subject can be authenticated by his/her face.

The controller (control means) 500 monitors an overall image supplied from the overall imaging device 100, and controls the guiding device (guiding means) 200, the illumination device (illumination means) 300, and the plurality of iris image pick-up devices (iris image pick-up means) 401 to 404. The functions of the controller 500 can be implemented by hardware or by a computer program(s). The controller 500 determines a start of biometric authentication for the subject based on his/her overall image supplied from the overall imaging device 100, or based on an external input.

The control performed by the controller 500 includes guiding control, illumination control, and iris image pick-up control. In the guiding control, the controller 500 supplies guiding control information for guiding the subject to the guiding device 200. The guiding device 200 guides the subject based on the guiding control information. The guiding device 200 includes, for example, a display and/or a speaker(s). For example, the guiding device 200 presents an image(s) and a sound(s) for indicating the start of biometric authentication through the display and/or the speaker, respectively. Further, the guiding device 200 presents images and sounds for inducing the subject to turn his/her eyes to the iris image pick-up devices through the display and/or the speaker, respectively.

In the illumination control, the controller 500 supplies, to the illumination device 300, illumination control information for applying illumination light to the subject. The illumination device 300 applies light (e.g., near-infrared light) to the subject based on the illumination control information. The illumination device 300 includes LEDs (Light Emitting Diodes) as a light source, and a synchronization signal generator. The amount of light applied from the illumination device 300 to the subject is determined by the value of the current supplied to the LEDs, the lighting time of the LEDs, and the lighting cycle thereof, and the illumination control information includes the numerical values thereof. When the LEDs are not continuously kept in the on-state, the lighting cycle of the LEDs is synchronized with the frame rates of the plurality of iris image pick-up devices 401 to 404.

In the iris image pick-up control, the controller 500 determines, based on the overall image supplied from the overall imaging device 100, one of the plurality of iris image pick-up devices 401 to 404 that can suitably photograph an area of the subject's eyes. Further, the controller 500 determines the vertical position of a region of interest that is read out at a high speed in the determined iris image pick-up device.

Figure 2:
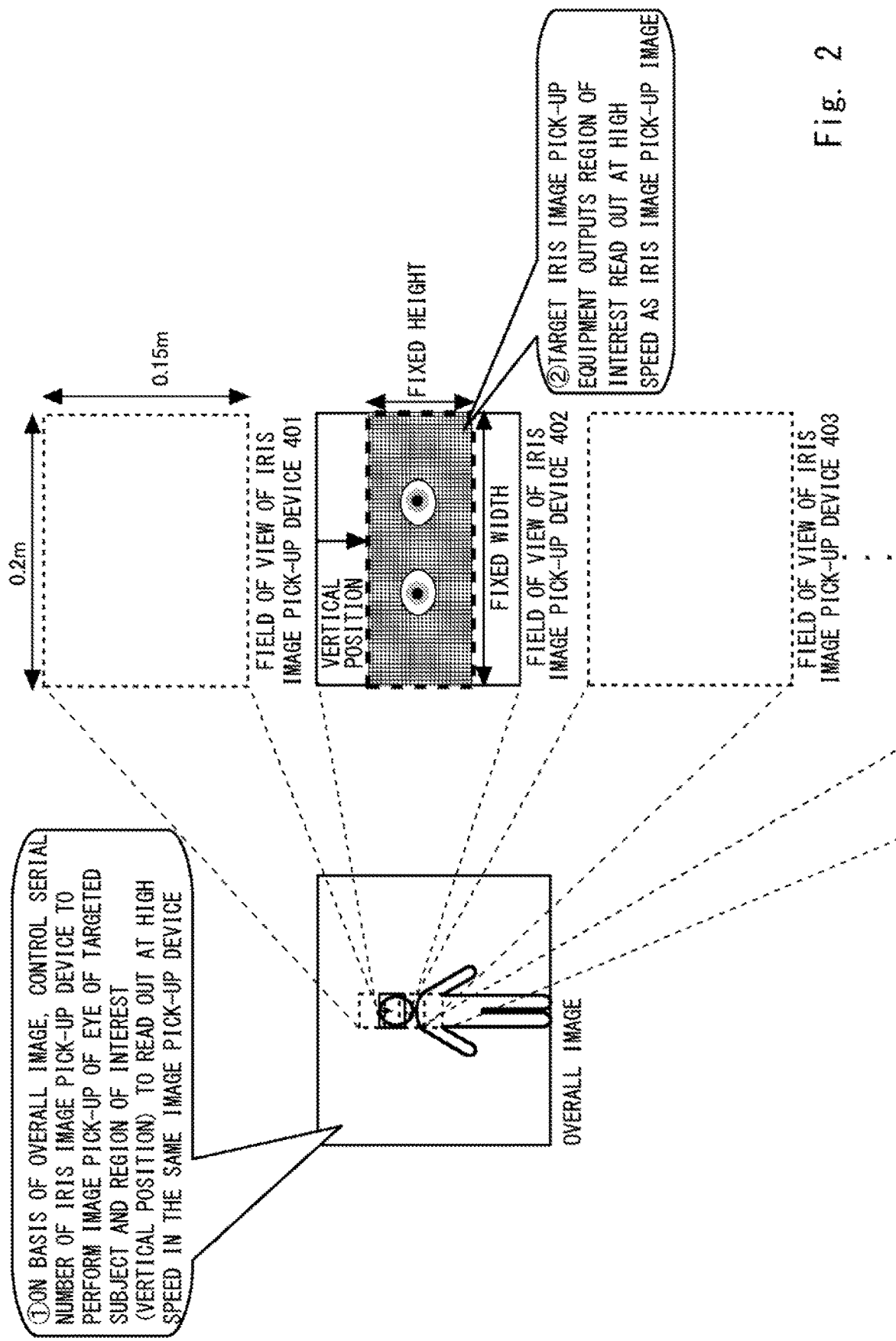
FIG. 2 shows a state of iris image pick-up control.

FIG. 2 shows a state of the iris image pick-up control. Details of the iris image pick-up control will be described with reference to FIG. 2. In this example, it is assumed that a general-purpose camera having 12M pixels (4,000 horizontal pixels and 3,000 vertical pixels) and a frame rate of 60 fps is used for each of the iris image pick-up devices 401 to 404. Such cameras have been becoming widespread as industrial cameras. In the case where the photographing is performed with a granularity of 50 µm, with which a subject can be authenticated by his/her iris, the horizontal and vertical fields of view of each of the iris image pick-up devices are 0.2 m (4,000×50 [µm]=0.2 [m]) and 0.15 m (3,000×50 [µm]=0.15 [m]), respectively.

The plurality of iris image pick-up devices 401 to 404 are arranged so that they are stacked on top of each other in the vertical direction. Note that the plurality of iris image pick-up devices 401 to 404 are arranged so that the image areas of iris image pick-up devices adjacent to each other partially overlap each other. For example, the iris image pick-up devices 401 to 404 are arranged so that the image areas of iris image pick-up devices adjacent to each other overlap each other by 2.5 cm. In such a case, at the focusing point 2 m away from the four iris image pick-up devices, they can secure a field of view of 0.2 m in the horizontal direction and 0.45 m ((0.15−0.025)+(0.15−0.025−0.025)+(0.15−0.025−0.025)+(0.15−0.025) m) in the vertical direction. That is, it is possible to secure the required field of view of 0.2 m in the horizontal direction and 0.4 m in the vertical direction. Note that it can be understood, by the drawings and the above description, that the iris image pick-up devices have the same fields of view as each other and are placed in positions different from each other.

In the case where the frame rate of each of the iris image pick-up devices is 60 fps, they cannot meet the required frame rate of 100 fps when they are used as they are. Note that an industrial camera or the like has a region-of-interest mode. In the region-of-interest mode, only a partial area that is defined as a region of interest is read out instead of reading out the entire area of the screen. It is possible to increase the frame rate by using such a region-of-interest mode.

The controller 500 sets a region of interest in any given iris image pick-up device and reads out the image in the region of interest from that iris image pick-up device. In the example shown in FIG. 2, a partial area of 4,000 pixels in the horizontal direction and 1,500 pixels in the vertical direction, which corresponds to a half of the entire area of the screen, is defined as the region of interest. In this case, since the number of pixels in each frame is a half of the number of pixels in the entire area, it is possible to increase the frame rate to 120 fps, which is twice the frame rate of 60 fps in the case where the entire area of the screen is read out. However, the horizontal and vertical fields of view of the partial area become 0.2 m and 0.75 m, respectively. Note that both eyes of a human being are aligned in the horizontal direction. Therefore, in the region-of-interest, it is preferred to reduce the number of pixels in the vertical direction, instead of reducing that in the horizontal direction, so that both eyes can be photographed.

Under the condition that the area of eyes is not photographed in the above-described range where the image areas of iris image pick-up devices adjacent to each other overlap each other, the iris image pick-up device that photographs the area of eyes is only one of the four iris image pick-up devices 401 to 404. Further, the condition under which the image can be read out at the frame rate of 120 fps is a partial area in that iris image pick-up device. The controller 500 infers one of the iris image pick-up devices 401 to 404 that can suitably photograph the area of eyes, and estimates the vertical position of the region of interest in which the image is read out at a high speed in that iris image pick-up device.

The above-described inference/estimation can be carried out by a method described below. The overall imaging device 100 has a resolution in which a subject can be authenticated by his/her face, and the controller 500 derives the positions of the eyes of the subject in the overall image taken by the overall imaging device 100. The controller 500 derives the iris image pick-up device corresponding to the positions of the eyes of the subject in the overall image and the positions of the eyes present in that imaging device by using camera parameters and the positional relation of the overall imaging device 100 and each of the iris image pick-up devices. By using the region-of-interest mode, it is possible, by using a general-purpose camera, to achieve a field of view wider than 0.2 m in the horizontal direction and 0.4 m in the vertical direction, and a temporal resolution higher than 100 fps.

Note that when the vertical position is changed in the above-described region-of-interest mode, a delay occurs before the start of the photographing. Therefore, in the above-described inference/estimation, an image that is obtained by photographing the subject at a position that is more distant than the position 2 meters away, i.e., more distant than the focusing point of the iris image pick-up device, e.g., by photographing the subject at a position 3 meters away may be used. The resolution in which a subject present at a position 3 meters away can be authenticated by his/her face can be achieved by a camera having about 2M pixels, so that cameras having specifications lower than those of the iris image pick-up cameras can be used for the overall imaging device 100.

The controller 500 supplies iris image pick-up information to each of the iris image pick-up devices 401 to 404 based on the above-described iris image pick-up control. The controller 500 supplies iris image pick-up information including the vertical position of the region of interest to the iris image pick-up device that photographs the area of the eyes of the subject. The controller 500 may supply optional iris image pick-up information to the other iris image pick-up devices. The controller 500 may supply iris image pick-up information including information about the stop of the supply of the iris image to the other iris image pick-up devices, for example, in order to reduce the total amount of the data of the iris image.

Each of the iris image pick-up devices 401 to 404 supplies the iris image to the controller 500 based on the iris image pick-up information supplied from the controller 500. Note that each of the iris image pick-up devices 401 to 404 outputs the image in the region of interest that is set by the controller 500 by using the iris image pick-up information (i.e., the iris image) to the controller 500. Each of the iris image pick-up devices 401 to 404 may lossy-compress the iris image in the region of interest and output the compressed iris image to the controller 500. For example, each of the iris image pick-up devices 401 to 404 compresses the iris image in the region of interest by using quantization (pixel-by-pixel compression), predictive coding and quantization (compression on a basis of a plurality of pairs of pixels), or a combination of transform coding and quantization (compression on a basis of a plurality of pairs of pixels). The controller 500 performs the authentication and the registration described in the background section by using the iris images supplied from the iris image pick-up devices 401 to 404. The controller 500 returns to the next process when there is a next subject or when the authentication or the registration has failed.

Figure 3:
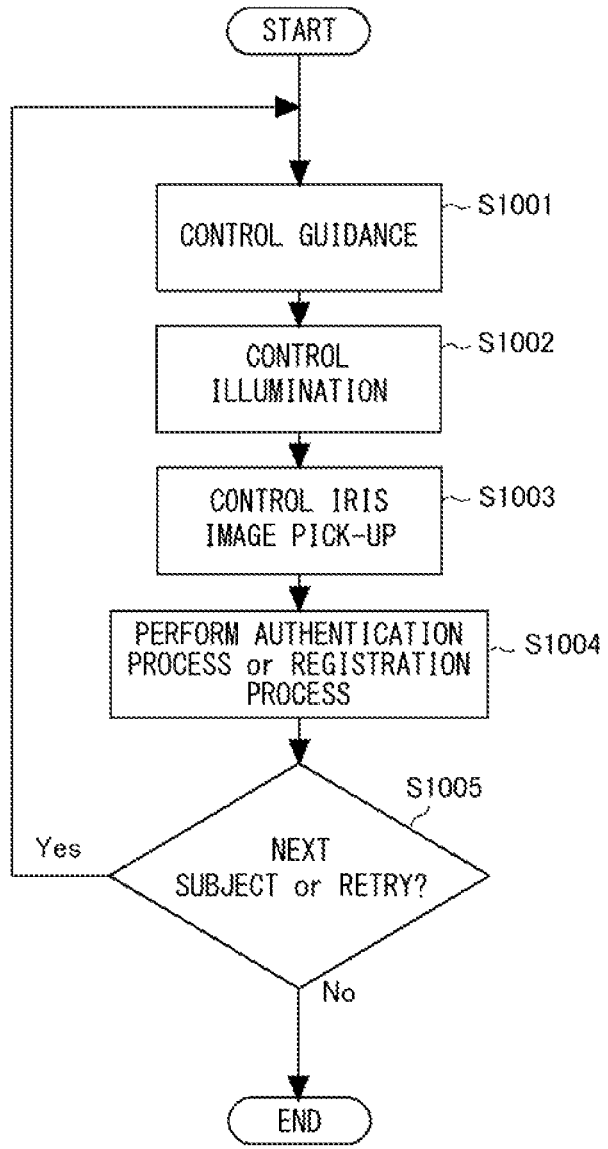
FIG. 3 is a flowchart showing an operational procedure in an image processing system.

Next, an operational procedure will be described. FIG. 3 shows an operational procedure in the image pick-up system. The controller 500 performs guiding control and thereby guides a subject by using the guiding device 200 (step S1001). The controller 500 performs the illumination control and thereby applies infrared light to the subject by using the illumination device 300 (step S1002). The controller 500 performs the above-described iris image pick-up control and thereby acquires an image(s) of an iris(es) (an iris image(s)) by using the plurality of iris image pick-up devices 401 to 404 (step S1003). The iris image(s) acquired in the step S1003 is used for the authentication or registration of the iris. In the step S1003, the controller 500 does not need to obtain the iris image from each of the iris image pick-up devices 401 to 404 for a given subject as described above. The controller 500 obtains the iris image from the iris image pick-up device that has photographed the area of the eyes of the subject.

The controller 500 performs iris-based authentication by using the iris image acquired in the step S1003, or registers the iris image (step S1004). The controller 500 determines whether or not there is a next subject, or whether or not re-authentication or re-registration should be performed (step S1005). When it is determined that there is a next subject, or re-authentication or re-registration should be performed, the process returns to the step S1001 and the process is performed starting from the guiding control.

Note that when the overall imaging device 100 according to this example embodiment has a resolution in which a subject can be authenticated by his/her face, and holds feature values for authenticating the subject by his/her face in a database but does not hold feature values for authenticating the subject by his/her iris in the database, the apparatus according to the present disclosure can also be used for a use in which the apparatus identifies a subject based on face-based authentication and registers extracted feature values of the iris(es) of the subject in the database. Further, the apparatus according to the present disclosure can also be used for a use in which the apparatus estimates information about the height of a subject based on information about the positions of the eyes obtained by the iris image pick-up control, or information about the positions of the eyes that is obtained when an iris image obtained by the iris image pick-up device is authenticated or registered, and registers the estimated information in the database. Further, the apparatus according to the present disclosure can be used, by using the estimated information about height, to determine or calibrate the vertical position of one of iris image pick-up devices that can suitably photograph the area of eyes and the region of interest in which the image is read out at a high speed in that iris image pick-up device.

In this example embodiment, a high resolution supporting the demanded 0.2 m×0.4 m field of view and a high frame rate performance corresponding to a time resolution of 0.01 s can be achieved with a combination of general-purpose cameras. As a result, it is easy to photograph an iris pattern at a level of quality sufficient for authentication and verification under conditions such as when there is a long distance between the subject and the image pick-up means, a wide field of view to be photographed, and the subject moves.

Next, a second example embodiment of the present disclosure will be described. The configuration of an overall image processing system according to this example embodiment may be similar to the configuration of the image processing system according to the first example embodiment illustrated in FIG. 1. In this example embodiment, the controller 500 also functions as an image processing apparatus that performs an image processing method. In this example embodiment, boards supporting direct memory access (DMA) transfer are used to connect the iris image pick-up devices 401 to 404 and the controller 500 through a high-speed interface.

Figure 4:
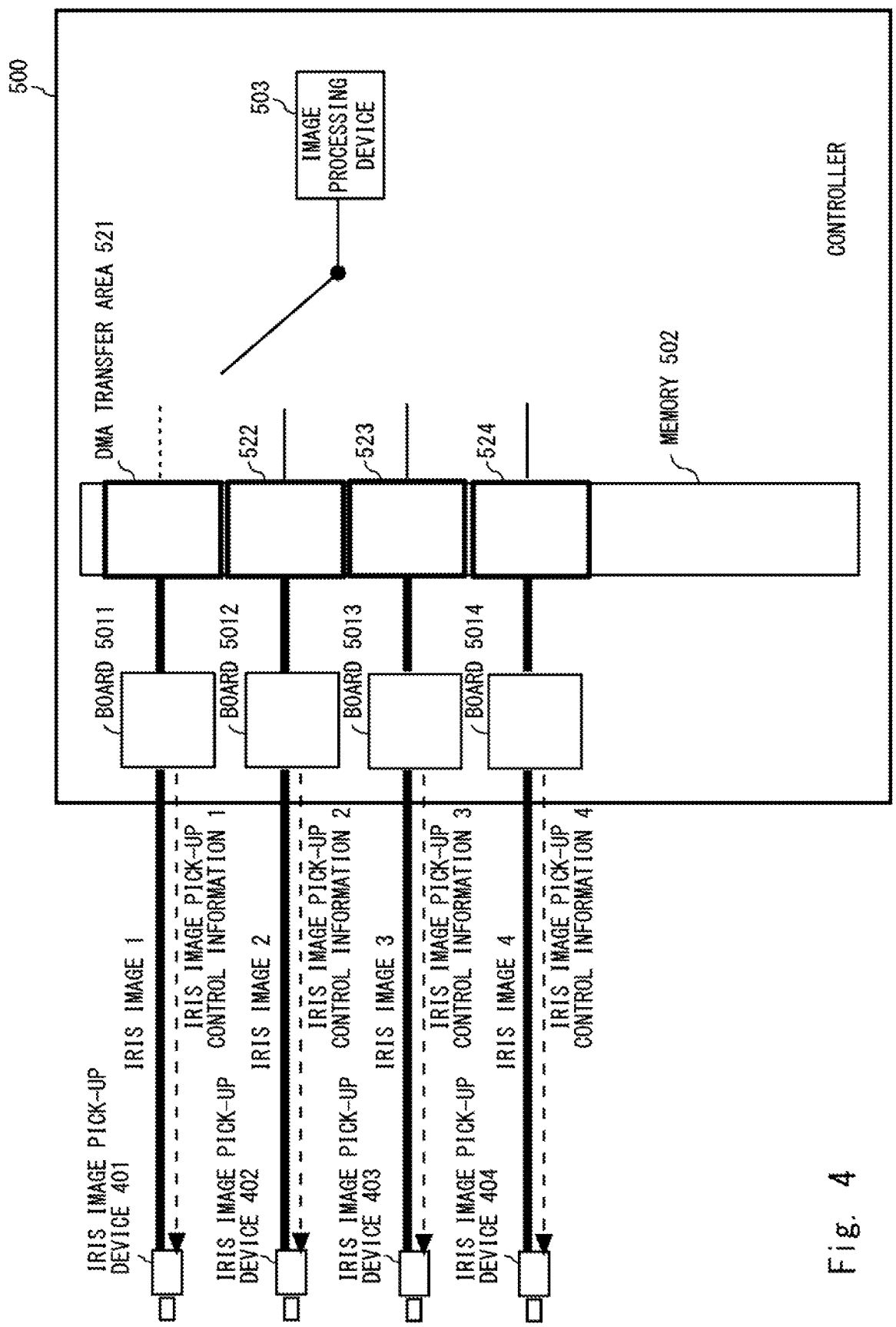
FIG. 4 is a block diagram showing a configuration of a controller used for investigation.

FIG. 4 illustrates the controller 500 used for investigation. The controller 500 includes boards 5011 to 5014 supporting DMA transfer, and an image processing unit 503. The boards 5011 to 5014 transfer images (iris images) read out from the iris image pick-up devices 401 to 404 to storage areas 521 to 524 designated for transfer (hereinafter also referred to as DMA transfer areas) in the memory 502 of the controller 500. With DMA transfers, iris images can be transferred to the DMA transfer areas 521 to 524 at high speeds, but there is limit to the capacity of the DMA transfer areas. The image processing unit 503 reads out iris images from the DMA transfer areas 521 to 524 in the memory 502, and performs various types of image processing and the like.

At this point, if attention is focused on fluctuations in the walking speed of the subject, the following problem occurs due to the capacity constraint on the DMA transfer areas described above. In the case of causing each iris image pick-up device to operate at a frame rate corresponding to the fastest walking speed, the number of images per unit time increases, thereby shortening the time of the iris images that can be recorded to the DMA transfer areas 521 to 524. In this case, there is a possibility that recording may end before a subject walking at the slowest walking speed passes through the focusing point of the iris image pick-up devices. Conversely, in the case of causing each iris image pick-up device to operate at a frame rate corresponding to the slowest walking speed, the time of the iris images that can be recorded to the DMA transfer areas 521 to 524 can be lengthened. However, in this case, there is a possibility that the iris image pick-up devices may be unable to capture the instant when the subject walking at the fastest walking speed passes through the focusing point. In either case, authentication and registration will fail.

Figure 5:
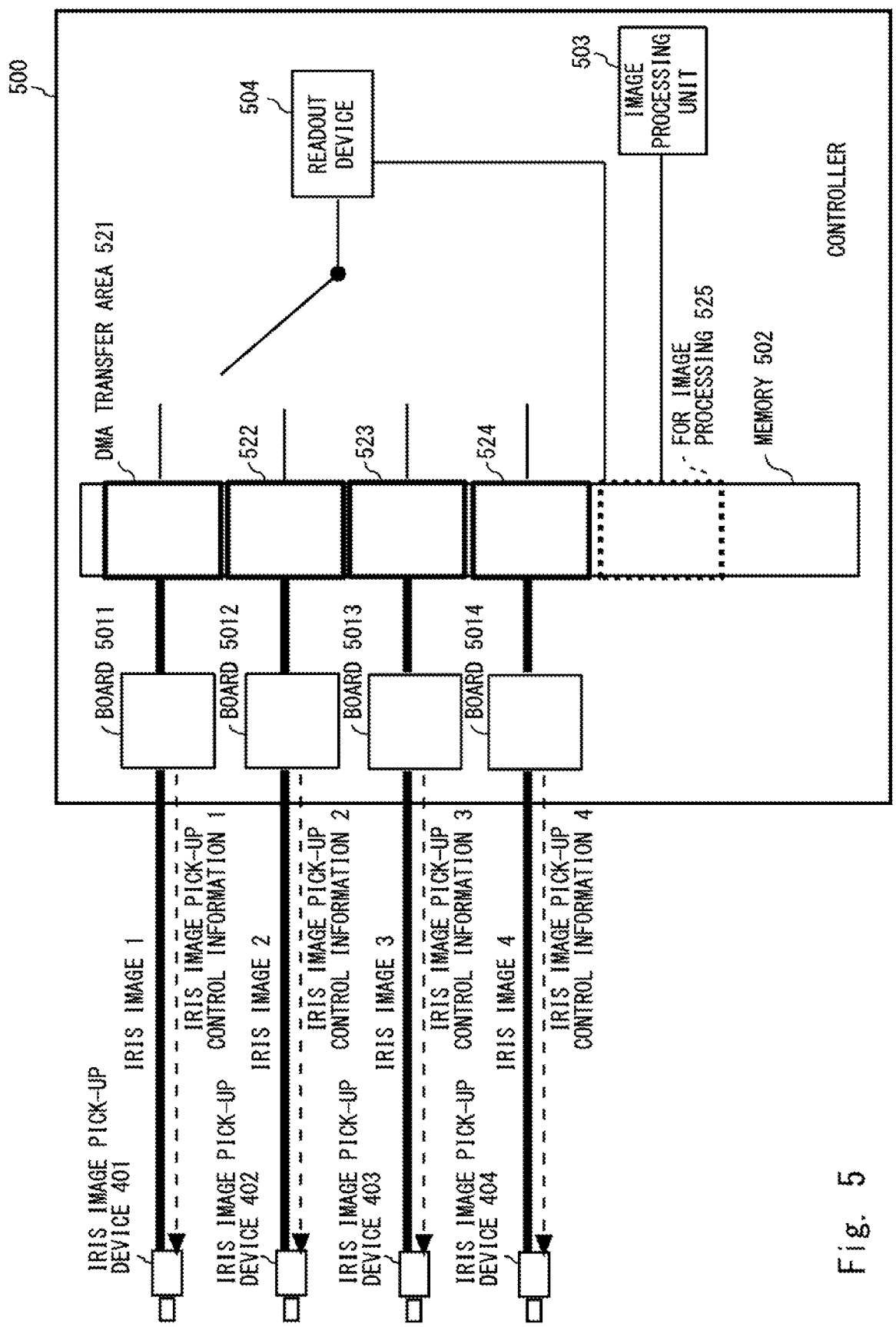
FIG. 5 is a block diagram showing a configuration of a controller used in a second example embodiment of the present disclosure.

FIG. 5 illustrates the controller 500 used in this example embodiment. The controller 500 includes a readout device 504 in addition to the components of the controller 500 illustrated in FIG. 4. Also, in the memory 502, a storage area 525 for image processing is provided in addition to the DMA transfer areas 521 to 524 corresponding to each board, independently of the DMA transfer areas. The readout device 504 reads out and transfers an iris image from one of the DMA transfer areas 521 to 524 to the storage area 525 for image processing. At this time, the readout device 504 reads out an iris image from one of the DMA transfer areas 521 to 524 at a frame interval according to the walking speed of the subject. The image processing unit 503 reads out an iris image from the storage area 525 for image processing, and performs various types of image processing and the like.

For example, by using an overall image pick-up device 100 including a distance measurement function such as time of flight (ToF), the controller 500 may analyze information about the distance to the subject as a time series and acquire information about the walking speed v [m/s]. The method of acquiring the walking speed of the subject is not particularly limited. For example, the controller 500 may also acquire information about the walking speed v [m/s] by analyzing the distance measured using a range sensor or the like in a time series.

In this example embodiment, the controller 500 causes each iris image pick-up device to operate at a frame rate max fps [fps] with which it is possible to capture the instant when a subject walking at the fastest walking speed max v [m/s] passes through the focusing point. Note that "frame rate" herein refers to the frame rate in the region-of-interest mode.

The controller 500 determines a frame interval of the DMA transfer areas at which to read out data to the memory area for image processing on the basis of the relationship between max v and the acquired walking speed v. For example, it is conceivable simply to derive max v÷v as the frame interval and cause the readout device 504 to perform a readout process according to this value. For example, in the case where the walking speed v is half the speed of max v, the frame interval is determined to be "2". In this case, the frame interval at which to read out data to the storage area 525 for image processing is lengthened, and therefore the recording time can be lengthened even with a limited memory area. Consequently, it is possible to prevent the recording from ending before a subject walking at a slow walking speed passes through the focusing point. At this time, the instant when the subject passes through the focusing point can also be picked up even though the time resolution has been reduced by an amount corresponding to the slowness of the walking speed.

Note that, as described in the first example embodiment, under conditions in which the eye region is not picked up in the range where the image pick-up regions of adjacent iris image pick-up devices overlap, the iris image pick-up device that picks up the eye region is only one of the four iris image pick-up devices 401 to 404. Consequently, it is sufficient if the storage area 525 for image processing used by the readout device 504 as a write destination has a capacity corresponding to a single camera. Even in the case where the eye region is picked up in the range where the image pick-up regions of adjacent iris image pick-up devices overlap, if the iris image picked up by one of the iris image pick-up devices is used, it is similarly sufficient if the storage area 525 for image processing has a capacity corresponding to a single camera.

In this example embodiment, if the time of the instant when the subject passes through the focusing point is known in addition to the walking speed of the subject, the controller 500 may also control the image pick-up start time in accordance with the time of the instant when the subject passes through the focusing point, instead of controlling the frame interval of the readout device 504. For example, the controller 500 may delay the start time of the readout from an iris image pick-up device such that the instant when a subject walking at a slow walking speed passes through the focusing point can be recorded.

In this example embodiment, the readout device 504 transfers iris images recorded to the DMA transfer areas 521 to 524 to the storage area 525 for image processing at a frame interval corresponding to the walking speed of the subject. This arrangement makes it possible to satisfy both the time resolution and the recording time for capturing the instant when the subject passes through the focusing point under the constraint of a limited storage area, even in the case where there are fluctuations in the walking speed of the subject.

Note that although an example in which a partial area of 4,000 pixels in the horizontal direction and 1,500 pixels in the vertical direction is defined as the region of interest in FIG. 2, the present disclosure is not limited to this example. The shape of the region of interest is not limited to the rectangle, and the number of region of interest s is not limited to one. The controller 500 may, for example, derive the positions of the right eye and left eye of the subject from the overall image (the overlooked image) taken by the overall imaging device 100, and set a region of interest corresponding to the position of the right eye and a region of interest corresponding to the position of the left eye in the iris image pick-up device. In such a case, the iris image pick-up device supplies iris images of the right and left eyes to the controller 500. The shape of the region of interest may be rectangular or may be elliptic. The controller 500 may derive the positions of the right and left eyes of the subject based on the iris image taken by the iris image pick-up device instead of based on the overlooked image. For example, the controller 500 may temporarily define the partial area shown in FIG. 2 as the region of interest, and derive the positions of the right and left eyes from the images in the region of interest. In such a case, the controller 500 may set, based on the derived positions of the right and left eyes, each of a partial area corresponding to the position of the right eye and a partial area corresponding to the position of the left eye as a region of interest in the iris image pick-up device.

Figure 6:
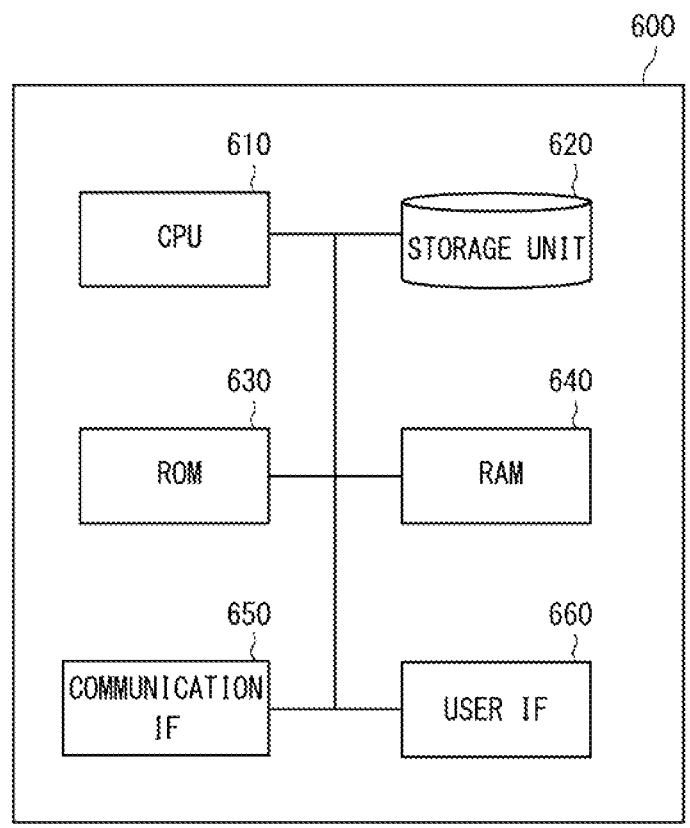
FIG. 6 is a block diagram showing an example of a configuration of a computer apparatus.

In each of above-described example embodiments, the controller 500 can be formed as a computer apparatus. FIG. 6 shows an example of a configuration of an information processing apparatus (a computer apparatus) that can be used for the controller 500. An information processing apparatus 600 includes a control unit (CPU: Central Processing Unit) 610, a storage unit 620, a ROM (Read Only Memory) 630, a RAM (Random Access Memory) 640, a communication interface (IF: Interface) 650, and a user interface 660.

The communication interface 650 is an interface for connecting the information processing apparatus 600 to a communication network through wired communication means, wireless communication means, or the like. The user interface 660 includes, for example, a display unit such as a display. Further, the user interface 660 includes an input unit such as a keyboard, a mouse, and a touch panel.

The storage unit 620 is an auxiliary storage device that can hold various types of data. The storage unit 620 does not necessarily have to be a part of the information processing unit 600, and may be an external storage device or a cloud storage connected to the information processing unit 600 through a network. The ROM 630 is a non-volatile storage device. For example, a semiconductor storage device such as a flash memory having relatively small capacity is used for the ROM 630. Programs executed by the CPU 610 can be stored in the storage unit 620 or the ROM 630.

The aforementioned program can be stored and provided to the information processing apparatus 600 by using any type of non-transitory computer readable media. Non-transitory computer readable media include any type of tangible storage media. Examples of non-transitory computer readable media include magnetic storage media such as floppy disks, magnetic tapes, and hard disk drives, optical magnetic storage media such as magneto-optical disks, optical disk media such as CD (Compact Disc) and DVD (Digital Versatile Disk), and semiconductor memories such as mask ROM, PROM (Programmable ROM), EPROM (Erasable PROM), flash ROM, and RAM. Further, the program may be provided to a computer using any type of transitory computer readable media. Examples of transitory computer readable media include electric signals, optical signals, and electromagnetic waves. Transitory computer readable media can provide the program to a computer via a wired communication line such as electric wires and optical fibers or a radio communication line.

The RAM 640 is a volatile storage device. As the RAM 640, various types of semiconductor memory apparatuses such as a DRAM (Dynamic Random Access Memory) or an SRAM (Static Random Access Memory) can be used. The RAM 640 can be used as an internal buffer for temporarily storing data and the like. The CPU 610 expands (i.e., loads) a program stored in the storage unit 620 or the ROM 630 in the RAM 640, and executes the expanded (i.e., loaded) program. By executing the program, the CPU 610 performs various types of control including, for example, guiding control, illumination control, and iris image pick-up control. Further, by the CPU 610 executing the program, various functions including, for example, at least one of the functions of the image processing unit 503 (refer to FIG. 5) or readout device 504 can be implemented.

Although example embodiments according to the present disclosure have been described above in detail, the present disclosure is not limited to the above-described example embodiments, and the present disclosure also includes those that are obtained by making changes or modifications to the above-described example embodiments without departing from the spirit of the present disclosure.

This application is based upon and claims the benefit of priority from Japanese patent application No. 2019-026939, filed on Feb. 18, 2019, the disclosure of which is incorporated herein in its entirety by reference.

REFERENCE SIGNS LIST

100 OVERALL IMAGING DEVICE
200 GUIDE DEVICE
300 ILLUMINATION DEVICE
401-404 IRIS IMAGE PICK-UP DEVICE
500 CONTROLLER
502 MEMORY
503 IMAGE PROCESSING UNIT
504 READOUT DEVICE
600 INFORMATION PROCESSING APPARATUS

What is claimed is:

1. An image processing system comprising:
a plurality of iris image pick-up cameras disposed at mutually different positions, each of the plurality of iris image pick-up cameras having a predetermined field of view;
an overall image pick-up camera configured to perform image pick-up over a wider field of view than the predetermined field of view;
a guiding device configured to guide a subject;
a light source configured to illuminate the subject with light;
a processor and
a memory storing instructions executable by the processor to:
using an image from the overall image pick-up camera, at least one of read out images from one or more of the iris image pick-up cameras, present at least one of an image and a sound through the guiding device, or provide illumination with the light from the light source;
write, to a first storage area for transfer, the images from the one or more of the iris image pick-up cameras;
read out the images from the first storage area at a frame interval corresponding to a movement speed of the subject;
write the read out images to a second storage area for image processing;
execute processing using the images written to the second storage area;
control an image pick-up start time of the one or more of the iris image pick-up cameras based on the movement speed of the subject and a time at which the subject passes through a focusing point of the one or more of the iris image pick-up cameras;
determine the frame interval to be a first frame interval when the movement speed of the subject is a first speed;
determine the frame interval to be a second frame interval longer than the first frame interval when the movement speed of the subject is a second speed slower than the first speed; and
delay, in a case where the movement speed of the subject is the second speed, a start time for reading out the images from the first storage area as compared to a case where the movement speed of the subject is the first speed.

2. The image processing system according to claim 1, wherein
the instructions are executable by the processor to further:
perform readout of the images from the one or more of the iris image pick-up cameras;
in performing the readout of the images from the one or more of the iris image pick-up cameras, specify the one or more of the iris image pick-up cameras as those of the image pick-up cameras that are capable of performing image pick-up of an eye of the subject based on the image acquired by the overall image pick-up cameras, set a region of interest including a position of the eye of the subject in the one or more of the iris image pick-up cameras, and acquire images of the region of interest from the one or more of the iris image pick-up cameras.

3. The image processing system according to claim 1, wherein
the instructions are executable by the processor to further:
write the images to the first storage area at a predetermined frame rate corresponding to a predetermined movement speed of the moving subject;
determine the frame interval according to a relationship between the predetermined movement speed and the movement speed of the moving subject; and
read out the images from the first storage area at the determined frame interval.

4. An image processing apparatus comprising:
a processor; and
a memory storing instructions executable by the processor to:
write, to a first storage area for transfer, images transferred from an iris image pick-up camera configured to perform image pick-up of an iris of a moving subject;
read out the images from the first storage area at a frame interval corresponding to a movement speed of the moving subject;
write the read out images to a second storage area for image processing;
execute processing using the images written to the second storage area;
control an image pick-up start time of the iris image pick-up camera based on the movement speed of the subject and a time at which the subject passes through a focusing point of the iris image pick-up camera;
determine the frame interval to be a first frame interval when the movement speed of the subject is a first speed;
determine the frame interval to be a second frame interval longer than the first frame interval when the movement speed of the subject is a second speed slower than the first speed; and
delay, in a case where the movement speed of the subject is the second speed, a start time for reading out the images from the first storage area as compared to a case where the movement speed of the subject is the first speed.

5. The image processing apparatus according to claim 4, wherein
the instructions are executable by the processor to further:
write the images to the first storage area at a predetermined frame rate corresponding to a predetermined movement speed of the moving subject;
determine the frame interval according to a relationship between the predetermined movement speed and the movement speed of the subject read out the images from the first storage area at the determined frame interval.

6. The image processing apparatus according to claim 5, wherein the frame interval is determined based on a ratio between the predetermined movement speed and the movement speed of the subject.

7. An image processing method comprising:
writing, by a processor and to a first storage area for transfer, images transferred from an iris image pick-up camera configured to perform image pick-up of an iris of a moving subject;
reading out, by the processor, the images from the first storage area at a frame interval corresponding to a movement speed of the moving subject;
writing, by the processor, the read out images to a second storage area for image processing;
executing, by the processor, processing using the images written to the second storage area;
controlling, by the processor, an image pick-up start time of the iris image pick-up camera based on the movement speed of the subject and a time at which the subject passes through a focusing point of the iris image pick-up camera; and
determining, by the processor, the frame interval to be a first frame interval when the movement speed of the subject is a first speed;
determining, by the processor, the frame interval to be a second frame interval which is longer than the first frame interval when the movement speed of the subject is a second speed which is slower than the first speed; and
delaying, by the processor, in a case where the movement speed of the subject is the second speed, a start time for reading out the images from the first storage area as compared to a case where the movement speed of the subject is the first speed.

* * * * *